(12) United States Patent
Wheatley et al.

(10) Patent No.: US 8,460,609 B1
(45) Date of Patent: *Jun. 11, 2013

(54) VENT STICK AIR FRESHENER WITH GRIP HEAD

(75) Inventors: Alan J. Wheatley, Draper, UT (US); Aaron Irvin, Salt Lake City, UT (US)

(73) Assignee: American Covers, Inc., Bluffdale, UT (US)

( * ) Notice: Subject to any disclaimer, the term of this patent is extended or adjusted under 35 U.S.C. 154(b) by 353 days.

This patent is subject to a terminal disclaimer.

(21) Appl. No.: 12/915,983

(22) Filed: Oct. 29, 2010

Related U.S. Application Data (63) Continuation-in-part of application No. 12/623,007, filed on Nov. 20, 2009, now Pat. No. 8,147,761, which is a continuation of application No. 11/264,670, filed on Oct. 31, 2005, now Pat. No. 7,687,037, which is a continuation-in-part of application No. 11/050,473, filed on Feb. 2, 2005, now abandoned, and a continuation-in-part of application No. 11/050,463, filed on Feb. 2, 2005, now Pat. No. 7,293,719, which is a continuation-in-part of application No. 10/786,385, filed on Feb. 24, 2004, now Pat. No. 7,137,570, said application No. 12/623,007 is a continuation of application No. 12/243,635, filed on Oct. 1, 2008, now Pat. No. 7,687,038, which is a continuation-in-part of application No. 11/264,670, filed on Oct. 31, 2005, now Pat. No. 7,687,037, which is a continuation-in-part of application No. 11/050,473, which is a continuation-in-part of application No. 11/050,463, which is a continuation-in-part of application No. 10/786,385.

(60) Provisional application No. 60/451,135, filed on Feb. 28, 2003, provisional application No. 60/517,030, filed on Nov. 3, 2003.

(51) Int. Cl.
*A62B 7/08* (2006.01)
*A61L 9/00* (2006.01)

(52) U.S. Cl.
USPC ............... 422/123; 422/120; 422/122; 422/5

(58) Field of Classification Search
USPC .................................... 422/120, 122, 123, 5
See application file for complete search history.

(56) References Cited

U.S. PATENT DOCUMENTS

| D176,671 S | 4/1876 | Myers |
| 369,878 A | 9/1887 | Palmer |

(Continued)

FOREIGN PATENT DOCUMENTS

| CA | 2077251 | 5/1993 |
| EP | 0 348 970 | 1/1990 |

(Continued)

OTHER PUBLICATIONS about.com Housekeeping, http://housekeeping.about.com/od/pr . . . affresh, Febreze Noticeables, accessed Oct. 2, 2008, 2 pages.

(Continued)

*Primary Examiner* — Regina M Yoo
(74) *Attorney, Agent, or Firm* — Thorpe North & Western LLP (57) ABSTRACT

An air freshener includes a fork body with a pair of vent rods and a polymer body coupled to a vent rod. A scent material is interspersed within the body. A head extends away from the pair of vent rods with indicia thereon and a pair of opposite finger grip surfaces is disposed on opposite sides of the head.

19 Claims, 6 Drawing Sheets

U.S. PATENT DOCUMENTS

| | | |
|---|---|---|
| 1,171,737 A | 2/1916 | Madigan |
| D140,109 S | 1/1945 | Pierce |
| 2,642,248 A | 6/1953 | Semon |
| 2,733,333 A | 1/1956 | Peters |
| D177,826 S | 5/1956 | Katz |
| D178,237 S | 7/1956 | Katz |
| 3,239,145 A | 3/1966 | Aurelio |
| 3,456,106 A | 7/1969 | Gluschkin |
| 3,552,632 A | 1/1971 | Wilson |
| 3,655,129 A | 4/1972 | Seiner |
| 3,847,305 A | 11/1974 | Tobin |
| 3,948,445 A | 4/1976 | Andeweg |
| 3,971,858 A | 7/1976 | Collier et al. |
| D246,986 S | 1/1978 | Costello |
| 4,084,079 A | 4/1978 | Costello |
| D250,041 S | 10/1978 | Schimanski |
| 4,149,675 A | 4/1979 | Van Breen et al. |
| 4,184,099 A | 1/1980 | Lindauer et al. |
| 4,226,944 A | 10/1980 | Stone et al. |
| D258,511 S | 3/1981 | Ashton |
| 4,280,649 A | 7/1981 | Montealegre |
| 4,301,949 A | 11/1981 | Palson et al. |
| 1,683,545 A | 9/1982 | Harris |
| 4,382,548 A | 5/1983 | van der Heijden |
| 4,391,781 A | 7/1983 | van Lit |
| 4,517,326 A | 5/1985 | Cordts et al. |
| 4,549,693 A | 10/1985 | Barlics |
| 4,594,380 A | 6/1986 | Chapin et al. |
| D286,323 S | 10/1986 | Haworth |
| 4,638,057 A | 1/1987 | Takahashi et al. |
| 4,649,046 A | 3/1987 | Kross |
| 4,703,070 A | 10/1987 | Locko et al. |
| RE32,834 E | 1/1989 | Cordts et al. |
| 4,808,347 A | 2/1989 | Dawn |
| 4,840,773 A | 6/1989 | Wade |
| 4,874,129 A | 10/1989 | DiSapio et al. |
| 4,880,690 A | 11/1989 | Szycher et al. |
| 4,950,542 A | 8/1990 | Barker |
| 4,968,456 A | 11/1990 | Muderlak et al. |
| 5,008,115 A | 4/1991 | Lee et al. |
| 5,019,434 A | 5/1991 | Matsumoto |
| 5,034,222 A | 7/1991 | Kellett et al. |
| 5,050,798 A | 9/1991 | Sullivan |
| D322,558 S | 12/1991 | Halm et al. |
| 5,071,704 A | 12/1991 | Fischel-Ghodsian |
| 5,114,625 A | 5/1992 | Gibson |
| 5,120,583 A | 6/1992 | Garcia |
| 5,178,327 A | 1/1993 | Palamand et al. |
| 5,180,107 A | 1/1993 | Lindauer |
| 5,193,445 A | 3/1993 | Ferguson |
| D334,975 S | 4/1993 | Bunce |
| 5,220,636 A | 6/1993 | Chang |
| D338,519 S | 8/1993 | Peterson |
| 5,234,162 A | 8/1993 | Sullivan |
| D349,157 S | 7/1994 | Rymer |
| D350,192 S | 8/1994 | Patel et al. |
| 5,368,822 A | 11/1994 | McNeil |
| 5,407,642 A | 4/1995 | Lord |
| 5,422,078 A | 6/1995 | Colon |
| D367,526 S | 2/1996 | Bignon |
| D367,924 S | 3/1996 | Patel et al. |
| 5,520,921 A | 5/1996 | Chalifoux |
| D373,626 S | 9/1996 | Dente et al. |
| D375,350 S | 11/1996 | Patel et al. |
| 5,595,194 A | 1/1997 | Talbot |
| D380,258 S | 6/1997 | Muller et al. |
| 5,651,522 A | 7/1997 | Davis et al. |
| 5,683,285 A | 11/1997 | Wong |
| 5,695,692 A | 12/1997 | Kennedy |
| 5,704,832 A | 1/1998 | Borrell |
| D390,941 S | 2/1998 | Cessaroni et al. |
| 5,725,152 A | 3/1998 | Akyu |
| 5,762,549 A | 6/1998 | Scheuer et al. |
| 5,780,527 A | 7/1998 | O'Leary |
| 2,794,767 A | 8/1998 | Wilson |
| 5,820,791 A | 10/1998 | Canale |
| D400,662 S | 11/1998 | Davis |
| 5,845,847 A | 12/1998 | Martin et al. |
| 5,860,552 A | 1/1999 | Culhane et al. |
| 5,861,128 A | 1/1999 | Vick et al. |
| D404,957 S | 2/1999 | Cheris et al. |
| 5,871,765 A | 2/1999 | Johnson et al. |
| 5,899,382 A | 5/1999 | Hayes et al. |
| D410,540 S | 6/1999 | Pinchuk |
| D415,267 S | 10/1999 | Kauzlarich et al. |
| 5,988,520 A | 11/1999 | Bitner |
| 6,044,202 A | 3/2000 | Junkel |
| D424,677 S | 5/2000 | Chen |
| D425,190 S | 5/2000 | Morikawa |
| 6,111,055 A | 8/2000 | Berger et al. |
| 6,123,906 A | 9/2000 | Farmer |
| D432,222 S | 10/2000 | Rymer et al. |
| D437,041 S | 1/2001 | Eisenbraun |
| 6,190,607 B1 | 2/2001 | Farmer |
| 6,191,197 B1 | 2/2001 | Wang et al. |
| 6,197,263 B1 | 3/2001 | Blount |
| 6,202,938 B1 | 3/2001 | Collier |
| D440,294 S | 4/2001 | Bilek |
| D441,441 S | 5/2001 | Upson |
| 6,264,887 B1 | 7/2001 | Farmer |
| 6,291,371 B1 | 9/2001 | Shefer et al. |
| 6,309,715 B1 | 10/2001 | Lindauer et al. |
| 6,325,475 B1 | 12/2001 | Hayes et al. |
| 6,357,260 B1 | 3/2002 | Lutz |
| 6,374,044 B1 | 4/2002 | Freidel |
| 6,375,966 B1 | 4/2002 | Maleeny et al. |
| 6,379,689 B1 | 4/2002 | Aguadisch |
| 6,391,398 B1 | 5/2002 | Pesu et al. |
| 6,416,043 B1 | 7/2002 | Elsenbraun |
| 6,514,467 B1 | 2/2003 | Bulsink et al. |
| D472,968 S | 4/2003 | Christianson |
| D478,379 S | 8/2003 | Talenton et al. |
| D478,973 S | 8/2003 | Wagner |
| D479,592 S | 9/2003 | Lammel et al. |
| D485,343 S | 1/2004 | Wu |
| D487,504 S | 3/2004 | Yuen |
| 6,712,286 B2 | 3/2004 | Baxter et al. |
| D488,214 S | 4/2004 | Quantin |
| D488,548 S | 4/2004 | Lablaine |
| D491,257 S | 6/2004 | Picken |
| D491,798 S | 6/2004 | Buthier |
| D496,720 S | 9/2004 | Dudley |
| 6,800,252 B1 | 10/2004 | Jedzinski |
| 6,830,733 B2 | 12/2004 | Stanley, III |
| 6,885,811 B2 | 4/2005 | He et al. |
| D504,943 S | 5/2005 | Dudley |
| D507,341 S | 7/2005 | Taylor |
| D511,568 S | 11/2005 | Wheatley |
| D514,679 S | 2/2006 | Wheatley |
| D515,192 S | 2/2006 | Smith et al. |
| 7,025,283 B2 | 4/2006 | Torres |
| 7,055,764 B1 | 6/2006 | Martinez et al. |
| 7,061,386 B2 | 6/2006 | Seresini |
| 7,137,570 B2 | 11/2006 | Wheatley et al. |
| D535,379 S | 1/2007 | Hundertmark |
| 7,159,792 B2 | 1/2007 | Wheatley et al. |
| D544,080 S | 6/2007 | Carlson |
| D544,594 S | 6/2007 | Zobele |
| D544,953 S | 6/2007 | Kee |
| D546,432 S | 7/2007 | Hundertmark |
| 7,243,859 B2 | 7/2007 | Caserta et al. |
| D550,345 S | 9/2007 | Weggelaar |
| D551,333 S | 9/2007 | Wu |
| 7,285,248 B2 | 10/2007 | Yamamoto et al. |
| D554,746 S | 11/2007 | Davis et al. |
| 7,293,719 B2 | 11/2007 | Wheatley |
| D565,162 S | 3/2008 | Carlson |
| 7,344,123 B2 | 3/2008 | Pankhurst et al. |
| D565,715 S | 4/2008 | Wu |
| D573,706 S | 7/2008 | Zlotnik et al. |
| D574,941 S | 8/2008 | Weggelaar |
| 7,441,360 B2 | 10/2008 | Christianson et al. |
| D580,039 S | 11/2008 | Zlotnik et al. |
| D585,129 S | 1/2009 | Huang |
| D585,971 S | 2/2009 | Carrizales |
| D591,415 S | 4/2009 | Wu |
| D593,670 S | 6/2009 | Valentiono et al. |

| | | | |
|---|---|---|---|
| D594,954 S | 6/2009 | Wheatley | |
| 7,544,332 B2 | 6/2009 | De Silva et al. | |
| D598,531 S | 8/2009 | Irvin | |
| D604,825 S | 11/2009 | Brandenburg | |
| D607,983 S | 1/2010 | Irvin | |
| 7,651,666 B2 | 1/2010 | Adair et al. | |
| 7,670,566 B2 | 3/2010 | Adair et al. | |
| 7,687,037 B2 | 3/2010 | Wheatley | |
| 7,687,038 B2 | 3/2010 | Wheatley | |
| 7,780,094 B2 | 8/2010 | Caserta et al. | |
| D629,881 S | 12/2010 | Valentino et al. | |
| D631,954 S | 2/2011 | Bertassi et al. | |
| D633,610 S | 3/2011 | Wu | |
| D640,781 S | 6/2011 | Brandenburg | |
| D642,668 S | 8/2011 | Lablaine | |
| D647,186 S | 10/2011 | Chan et al. | |
| D649,237 S | 11/2011 | Bilko et al. | |
| 8,147,761 B2 * | 4/2012 | Wheatley et al. | 422/123 |
| D667,100 S | 9/2012 | Hakim | |
| 2001/0051234 A1 | 12/2001 | Ryan et al. | |
| 2003/0097936 A1 | 5/2003 | Maleeny et al. | |
| 2003/0199421 A1 | 10/2003 | Copfer | |
| 2004/0197221 A1 | 10/2004 | Stanley, III | |
| 2004/0265164 A1 | 12/2004 | Woo et al. | |
| 2005/0084413 A1 | 4/2005 | Stanley, III | |
| 2005/0127538 A1 | 6/2005 | Fabrega et al. | |
| 2005/0169793 A1 | 8/2005 | Wheatley et al. | |
| 2006/0043216 A1 | 3/2006 | Robinson | |
| 2006/0078477 A1 | 4/2006 | Althouse et al. | |
| 2006/0279008 A1 | 12/2006 | Jursich | |
| 2007/0057084 A1 | 3/2007 | Vieira | |
| 2007/0160492 A1 | 7/2007 | Spector | |
| 2007/0231508 A1 | 10/2007 | Fand et al. | |
| 2007/0290064 A1 | 12/2007 | Majerowski et al. | |
| 2008/0099576 A1 | 5/2008 | Hart | |
| 2008/0128925 A1 | 6/2008 | Pankhurst et al. | |
| 2008/0311315 A1 | 12/2008 | Marlow | |
| 2008/0311316 A1 | 12/2008 | Marlow | |
| 2009/0008411 A1 | 1/2009 | Schumacher et al. | |
| 2009/0010813 A1 | 1/2009 | Wang et al. | |
| 2009/0173799 A1 | 7/2009 | Litten-Brown et al. | |
| 2010/0010409 A1 | 1/2010 | Irvin | |
| 2010/0019059 A1 | 1/2010 | Bulsink et al. | |
| 2010/0065654 A1 | 3/2010 | Wheatley et al. | |
| 2010/0187327 A1 | 7/2010 | Irvin | |
| 2011/0108632 A1 | 5/2011 | Brandenburg et al. | |

FOREIGN PATENT DOCUMENTS

| | | |
|---|---|---|
| EP | 1 346 734 | 9/2003 |
| WO | WO 98/46284 | 10/1998 |
| WO | WO 00/24434 | 5/2000 |
| WO | WO 00/64498 | 11/2000 |
| WO | WO 02/35975 | 5/2002 |
| WO | WO 02/38029 | 5/2002 |
| WO | WO 2004/078219 | 9/2004 |
| WO | WO 2006/010282 | 2/2006 |
| WO | WO 2006/084160 | 8/2006 |
| ZA | 20004637 | 9/2000 |

OTHER PUBLICATIONS

Aromate E-News, Innovation in Novelty Fragrance, Http://209.85.173.104/seasrch?qcach . . . , accessed Oct. 8, 2008, 2 pages.
ecrater, www.ecrater.com/product.hp? . . . , Yankee Candle Selects Two Scents Electric Fragrance Unit Macintosh/Home Sweet Home, accessed Oct. 2, 2008, 1 page.
http://decomodo.com/articles/categor/lighting/, Bamboo Pillar Candle, Jan. 8, 2008, 1 page.
http://shop.advanceautoparts.com/webapp/wcs/stores/servlet/product_6170795-P_N3004 . . . Advance Auto Part; Arometrics Dual-Scent Vent—Juicy Strawberry and Vanilla; 1 Page; accessed Dec. 10, 2010.
http://www.bestliquidations.com/Medo_Vent Frehser.htm; BestLiquidations.com; Medo Vent Fresh Air Fresheners; 2 pages; accessed Dec. 10, 2010.
Medo® Air Fresheners; Auto Expressions™ 2005 Product Catalog; 25 pages.
Pictures (3) of Medo® auto Expressions Vent™ Air Freshener distributed by SOPUS Products of Moorpark , CA 2003 copyright date on package.
Scents & Sprays, www.scentsandsprays.com/ya . . . , Yankee Autumn Bounty Electric 2 Home Air Fresheners, copyright 2001-2008 scentsandsprays.com, accessed Oct. 2, 2008, 1 page.
U.S. Appl. No. 12/378,121, filed Oct. 29, 2010; Aaron Irvin.
U.S. Appl. No. 12/915,924, filed Oct. 29, 2010; Nathaniel Finlay.
U.S. Appl. No. 12/916,038, filed Oct. 29, 2010; Aaron Irvin.
U.S. Appl. No. 12/979,763, filed Dec. 28, 2010; Aaron Irvin.
U.S. Appl. No. 12/979,795, filed Dec. 28, 2010; Arron Irvin.
U.S. Appl. No. 12/979,813, filed Dec. 28, 2010; Aaron Irvin.
U.S. Appl. No. 13/009,574, filed Jan. 19, 2011; Alan J. Wheatley.
U.S. Appl. No. 29/378,112, filed Oct. 29, 2010; Nathaniel Finlay.
U.S. Appl. No. 29/378,116, filed Oct. 29, 2010; Aaron Irvin.
www.4imprint.com/EXEC/DETAIL/FROMPRODUCTGROUP/~SKU100300/~CA100300.htm, Hot Rod Vent Stick Air Freshener (it . . . , accessed Aug. 12, 2008, 2 pages.
www.autothing.com/Products/Air%20Fresheners/air%20freshener-clip.htm, Air Fresheners, Fresh Scents for you mobile Life, Clip-on Air Vent Clips rom Eagle o., Accessed Aug. 12, 2008, 1 page.
www.chicscents.com/Products.aspx Island Adventure Sandals; 2 pages; accessed Feb. 1, 2011.
www.chicscents.com/Products.aspx; Inspiration 3-D by Chic; 2 pages; accessed Feb. 1, 2011.
U.S. Appl. No. 12/623,007, filed Nov. 20, 2009; Alan J. Wheatley; Notice of Allowance issued Nov. 28, 2012.
U.S. Appl. No. 13/282,035, filed Oct. 26, 2011; Nathaniel Finlay.
U.S. Appl. No. 13/281,890, filed Oct. 26, 2011; Aaron Irving.
U.S. Appl. No. 29/378,112, filed Oct. 29, 2010; Nathaniel Finlay; Notice of Allowance issued Mar. 29, 2012.
U.S. Appl. No. 12/916,038, filed Oct. 29, 2010; Aaron Irvin; Notice of Allowance issued Apr. 27, 2012.
U.S. Appl. No. 29/415,358, filed Mar. 9, 2012; Aaron Irvin; Notice of Allowance issued May 29, 2012.
U.S. Appl. No. 12/693,543, filed Jan. 26, 2010; Aaron Irvin; office action dated Aug. 7, 2012.
U.S. Appl. No. 12/623,007, filed Nov. 20, 2009; Alan J. Wheatley; office action issued Jul. 29, 2011.
U.S. Appl. No. 29/394,683, filed Jun. 20, 2011; Alan J. Wheatley; notice of allowance issued Aug. 22, 2011.
U.S. Appl. No. 13/191,966, filed Jul. 27, 2011; Aaron Irvin.
U.S. Appl. No. 12/979,813, filed Dec. 28, 2010; Aaron Irvin; office action dated Sep. 14, 2012.
U.S. Appl. No. 12/979,795, filed Dec. 28, 2010; Aaron Irvin; office action dated Sep. 13, 2012.
U.S. Appl. No. 12/979,763, filed Dec. 28, 2010; Aaron Irvin; office action dated Dec. 14, 2012.
U.S. Appl. No. 12/693,543; filed Jan. 26, 2010; Aaron Irvin; office action dated Dec. 18, 2012.
U.S. Appl. No. 12/979,795; filed Dec. 28, 2010; Aaron Irvin; office action dated Jan. 28, 2013.
U.S. Appl. No. 13/009,574; filed Jan. 19, 2011; Alan J. Wheatley; office action dated Jan. 11, 2013.
U.S. Appl. No. 12/979,813; filed Dec. 28, 2010; Aaron Irvin; office action dated Jan. 31, 2013.
U.S. Appl. No. 29/435,389; filed Oct. 23, 2012; Aaron Irvin; notice of allowance dated Mar. 1, 2013.
U.S. Appl. No. 12/987,662; filed Jan. 10, 2011; Alan J. Wheatley; office action dated Mar. 21, 2013.
U.S. Appl. No. 12/979,601; filed Dec. 28, 2010; Alan J. Wheatley; office action dated Mar. 1, 2013.
U.S. Appl. No. 13/359,726; filed Jan. 27, 2012; Aaron Irvin; office action dated Apr. 5, 2013.

* cited by examiner

VENT STICK AIR FRESHENER WITH GRIP HEAD

PRIORITY CM

This is a continuation-in-part of U.S. patent application Ser. No. 12/623,007, filed on Nov. 20, 2009; now U.S. Pat. No. 8,147,761 which is a continuation of U.S. patent application Ser. No. 11/264,670, filed Oct. 31, 2005, now U.S. Pat. No. 7,687,037; which is a continuation-in-part application of U.S. patent application Ser. No. 11/050,473, filed Feb. 2, 2005, now abandoned and Ser. No. 11/050,463, filed Feb. 2, 2005, now U.S. Pat. No. 7,293,719; both of which are continuation-in-part applications of U.S. patent application Ser. No. 10/786,385, filed Feb. 24, 2004, now U.S. Pat. No. 7,137,570, which claims the benefit of U.S. Provisional Application Ser. Nos. 60/451,135, filed Feb. 28, 2003, and 60/517,030, filed Nov. 3, 2003; all of which are herein incorporated by reference.

This is a continuation-in-part of U.S. patent application Ser. No. 12/623,007, filed on Nov. 20, 2009; now U.S. Pat. No. 8,147,761 which is a continuation of U.S. patent application Ser. No. 12/243,635, filed Oct. 1, 2008, now U.S. Pat. No. 7,687,038; which is a continuation-in-part of U.S. patent application Ser. No. 11/264,670, filed Oct. 31, 2005, now U.S. Pat. No. 7,687,037; which is a continuation-in-part of U.S. patent application Ser. No. 11/050,473, now abandoned and Ser. No. 11/050,463, filed Feb. 2, 2005, now U.S. Pat. No. 7,293,719; both of which are continuation-in-parts of U.S. patent application Ser. No. 10/786,385, filed Feb. 24, 2004, now U.S. Pat. No. 7,137,570, which claims the benefit of U.S. Provisional Application Ser. Nos. 60/451,135, filed Feb. 28, 2003, and 60/517,030, filed Nov. 3, 2003; all of which are herein incorporated by reference.

RELATED PATENT(S)/APPLICATION(S)

This is related to U.S. patent application Ser. No. 10/786,385, filed Feb. 24, 2004, now U.S. Pat. No. 7,137,570; and U.S. patent application Ser. No. 11/050,463, filed Feb. 2, 2005, now U.S. Pat. No. 7,293,719; and U.S. patent application Ser. No. 11/290,334, filed Nov. 29, 2005, now U.S. Pat. No. 7,159,792.

BACKGROUND

1. Field of the Invention

The present invention relates generally to air fresheners.

2. Related Art

Vent rod type air fresheners typically have a pair of rods that are insertable into an air vent. For example, see U.S. Pat. Nos. 6,190,607; 6,123,906 and 6,264,887. Some can have a strip attached to a frame. For example, see U.S. Pat. No. 6,416,043.

SUMMARY OF THE INVENTION

It has been recognized that it would be advantageous to develop a vent rod style air freshener that is easier to grasp.

The invention provides an air freshener device in combination with a grill of an air vent through which air is forced. The air freshener includes a fork body having a pair of vent rods extending through the grill. A gap is between the pair of vent rods. An enlarged genesis of the gap is enlarged with respect to the gap. A pair of coherent elastomeric polymer bodies is each coupled to a different one of the pair of vent rods, and extends through the grill with the pair of vent rods, and each facing away from the gap. A scent material is interspersed within the pair of bodies and is capable of diffusing out of the pair of bodies to surrounding air. A head extends away from the pair of vent rods with the head adjacent the grill and has indicia thereon. A pair of opposite finger grip surfaces are disposed on opposite sides of the head parallel with one another and having a depth aligned with the pair of vent rods that is equal to or greater than a width or a height of the pair of vent rods, and a width at least substantially equal to the width of the pair of vent rods. Each of the pair of opposite finger grip surfaces has at least one rib extending therefrom, or at least one channel penetrating therein, and oriented transverse to the pair of vent rods.

In accordance with another aspect, the invention provides an air freshener device in combination with a grill of an air vent through which air is forced. The air freshener includes a fork body having a pair of vent rods extending through the grill. At least one coherent elastomeric polymer body is coupled to at least one of the pair of vent rods, and extends through the grill with the pair of vent rods. A scent material is interspersed within the body and is capable of diffusing out of the body to surrounding air. A head extends away from the pair of vent rods with the head adjacent the grill and has indicia thereon. A pair of opposite finger grip surfaces is disposed on opposite sides of the head and has a depth aligned with the pair of vent rods that is equal to or greater than a width or a height of the pair of vent rods.

In accordance with another aspect, the invention provides an air freshener device including a head with indicia. A clip is coupled to the head and extends perpendicularly outward from the head. The clip is sized and shaped to be inserted into a vehicle air vent and clipped to a vehicle air vent cover such that the head is adjacent the vehicle air vent. The clip includes a pair of vent rods sized and shaped to be inserted into the vehicle air vent and has a plurality of protrusions. A pair of coherent elastomeric polymer bodies has a plurality of apertures, with each of the bodies coupled to a different one of the vent rods via coupling of the plurality of apertures with the plurality of protrusions. The polymer bodies are insertable into the vehicle air vent with the vent rods. A scent material is interspersed within the bodies and is capable of diffusing out of the bodies to surrounding air. A pair of opposite finger grip surfaces is disposed on opposite sides of the head with protrusions or indentations or both to assist gripping the finger grip surfaces.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 1b is a perspective view of the air freshener device of FIG. 1a;

FIG. 2 is a side view of the air freshener device of FIG. 1a;

FIG. 3 is a top view of the air freshener device of FIG. 1a;

FIG. 4a is an exploded side view of the air freshener device of FIG. 1a;

FIG. 4b is an exploded perspective view of the air freshener device of FIG. 1a;

FIG. 7a is a perspective cross-sectional view of the air freshener device of FIG. 1a;

FIG. 7b is a side cross-sectional view of the air freshener device of FIG. 1a;

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Figure 1A:
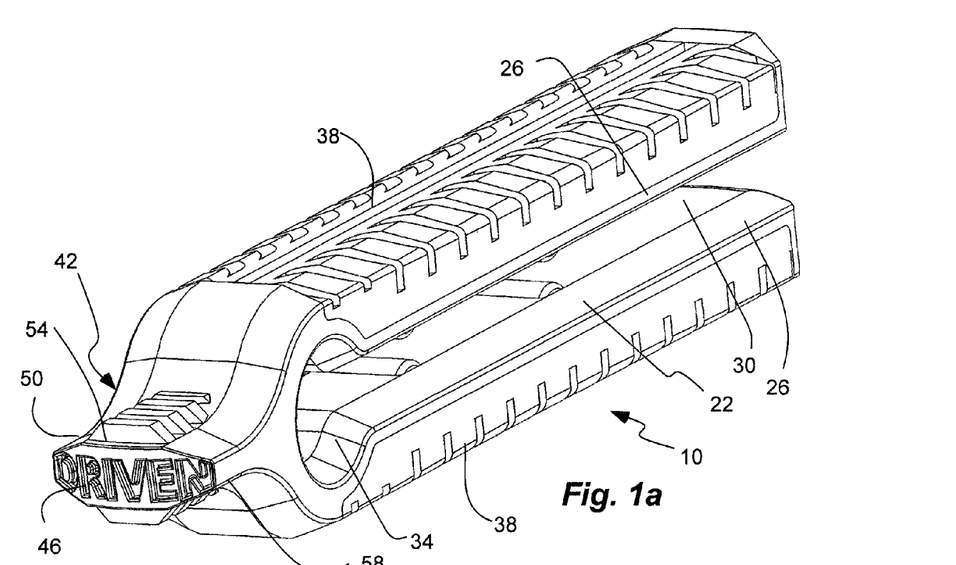
FIG. 1a is a perspective view of an air freshener in accordance with an embodiment of the present invention.
Figure 1B:
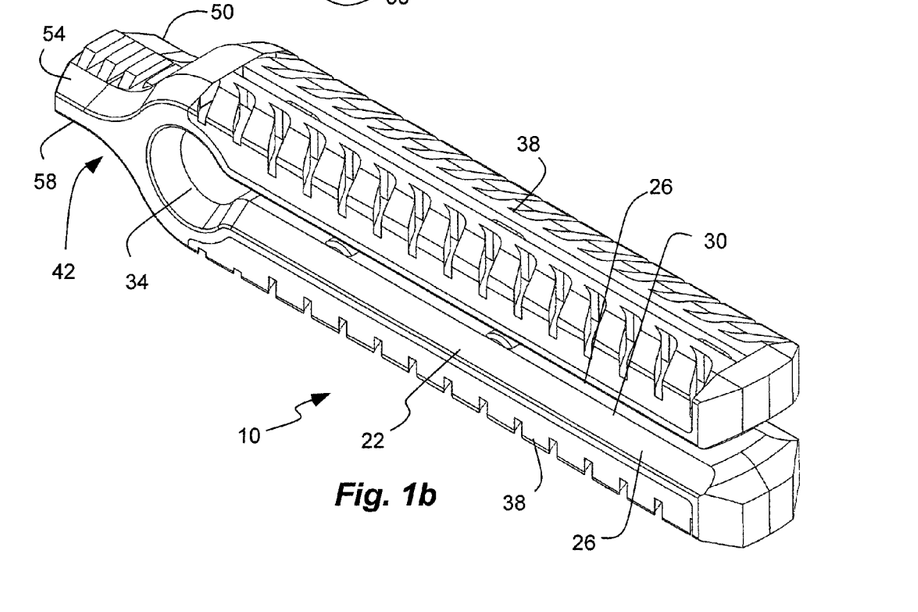

As illustrated in FIG. 1, an air freshener device, indicated generally at 10, in an example implementation in accordance with the invention is shown utilized with a grill 14 of an air vent 18 providing forced air or an air flow. For example, the grill and air vent can be associated with a vehicle. As another example, the air vent can be associated with a building ventilation system. The grill can define a cover of the air vent. The air freshener can provide a desired and/or aesthetically pleasing scent, fragrance, aroma or neutralizing agent. Air fresheners are one example of a field that can benefit from the present invention.

The air freshener 10 has a fork or forked body 22 with a pair of vent rods 26 that extend through the grill 14 of the air vent 18. The vent rods 26 can be oriented generally horizontal in use, and vertically oriented with respect to one another, with one disposed over the other, forming upper and lower vent rods. A gap 30 is defined between the vent rods and can receive part of the grill therein. The gap can also be oriented generally horizontal in use with a vent rod above and a vent rod below. The vent rods 26 can have a majority that is flat and thin, having a height or thickness $t_{vr}$ less than a width $w_{vr}$ of the vent rods. The thickness of the majority of the vent rods is measured perpendicularly to the gap, while the width is measured perpendicularly to a length of the vent rods or longitudinal axis 32 of the air freshener. The width of the vent rod can be the same as a width $w_{af}$ of the air freshener. The air freshener can have a width $w_{af}$ that is constant along substantially the entire length L of the air freshener. The forked body and vent rods can be formed of plastic, and can be manufactured by injection molding. The pair of vent rods form a clip for engaging the grill of the air vent.

Figure 2:
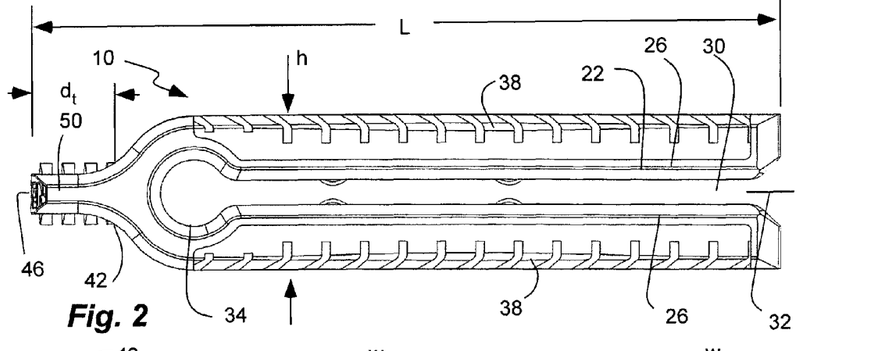
Figure 3:
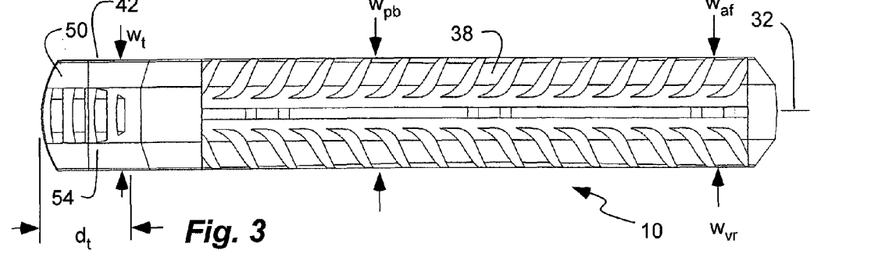

The gap 30 can include an enlarged genesis 34 at an end of the gap at the head. The genesis 34 is enlarged with respect to the gap 30, or has a thickness $t_b$ thicker than a thickness $t_g$ of the gap between the vent rods. The genesis 34 can have a circular or round shape, oriented vertically, with a diameter d equal to the genesis thickness $t_b$ and greater than the gap thickness $t_g$. The genesis diameter or thickness can also be greater than a thickness $t_o$ between opposite outer surfaces of the vent rods. The curvature of the genesis can reduce stress concentrations when the vent rods bend outwardly around the grill.

Figures 5A, 6:
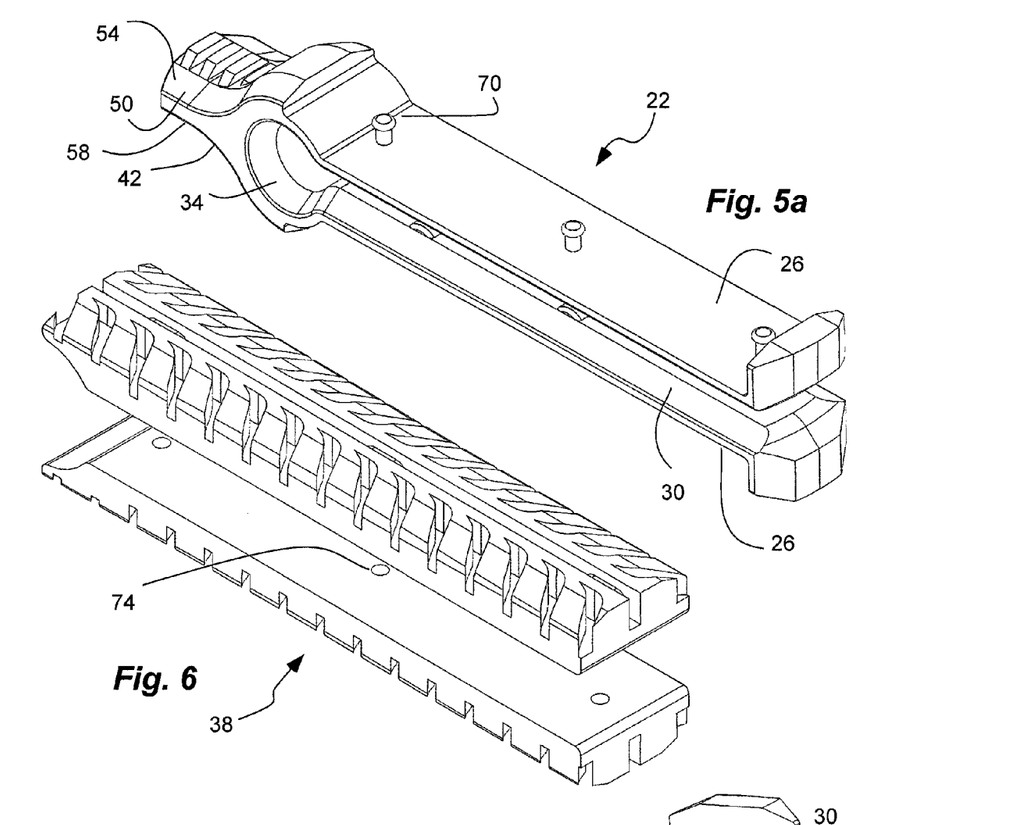
FIG. 5a is a perspective view of a vent clip of the air freshener device of FIG. 1a with the pair of coherent elastomeric polymer bodies removed.
FIG. 6 is a perspective view of a pair of coherent elastomeric polymer bodies of the air freshener device of FIG. 1a with the vent clip removed.
Figure 5B:
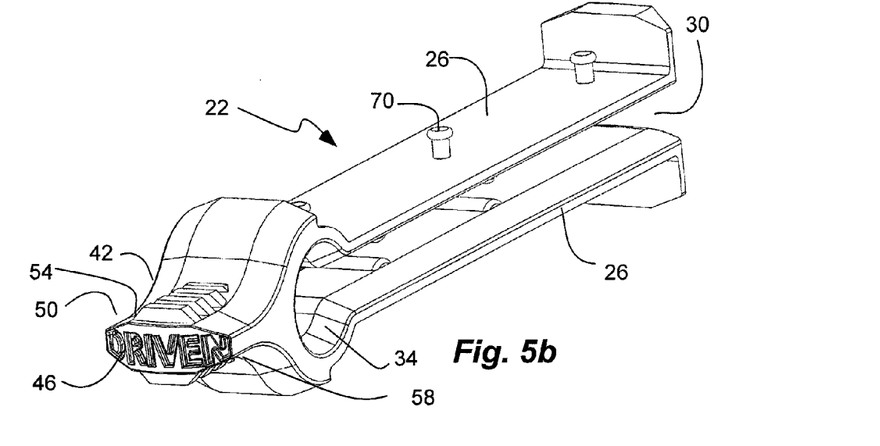
FIG. 5b is a perspective view of the vent clip of the air freshener device of FIG. 1a with the pair of coherent elastomeric polymer bodies removed.
Figure 7A:
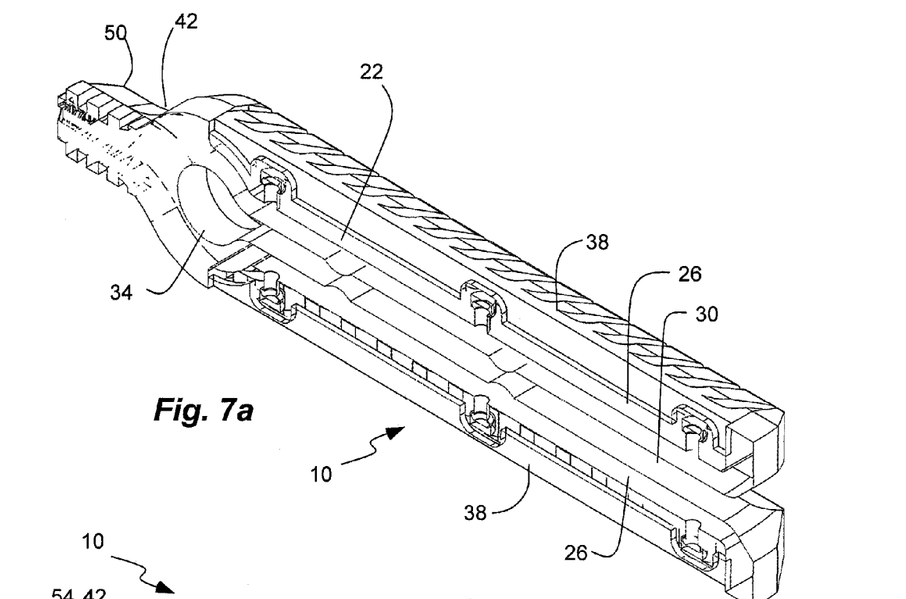
Figure 7B:
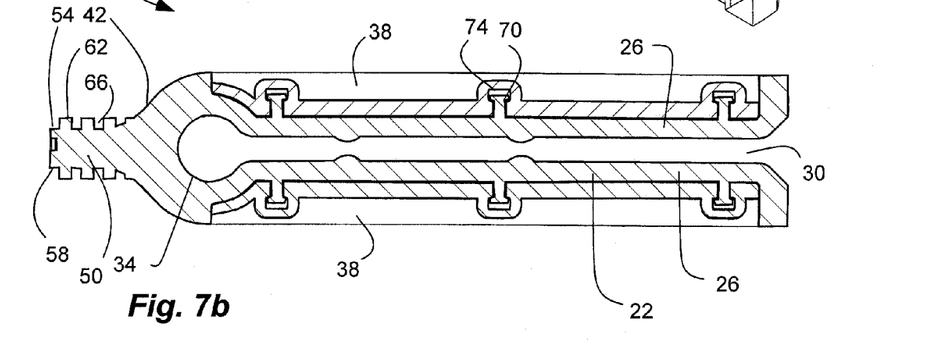
Figure 8A:
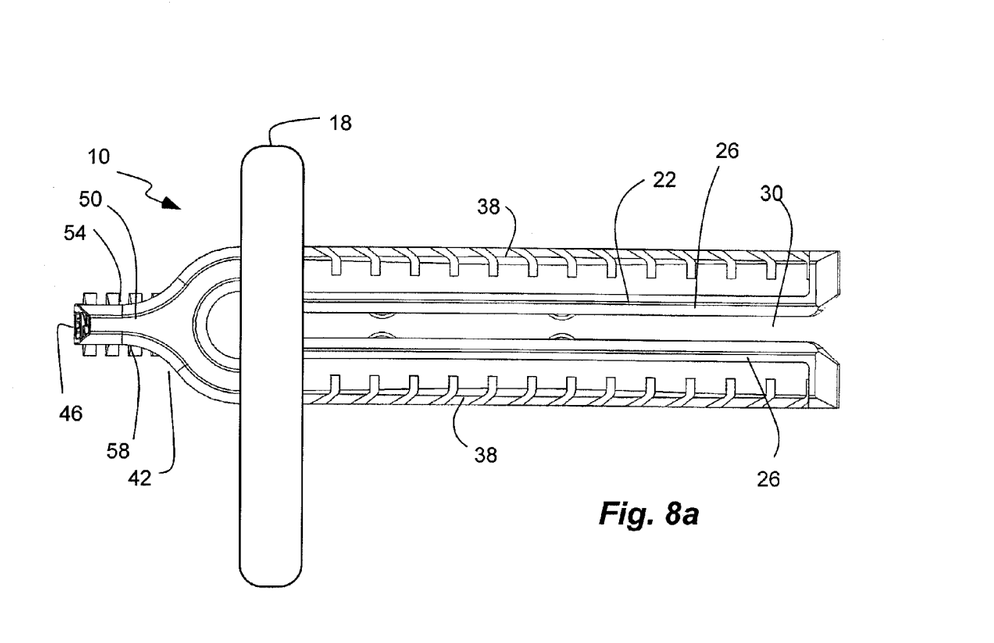
FIG. 8a is a side view of the air freshener device of FIG. 1a utilized with a grill of an air vent.
Figure 8B:
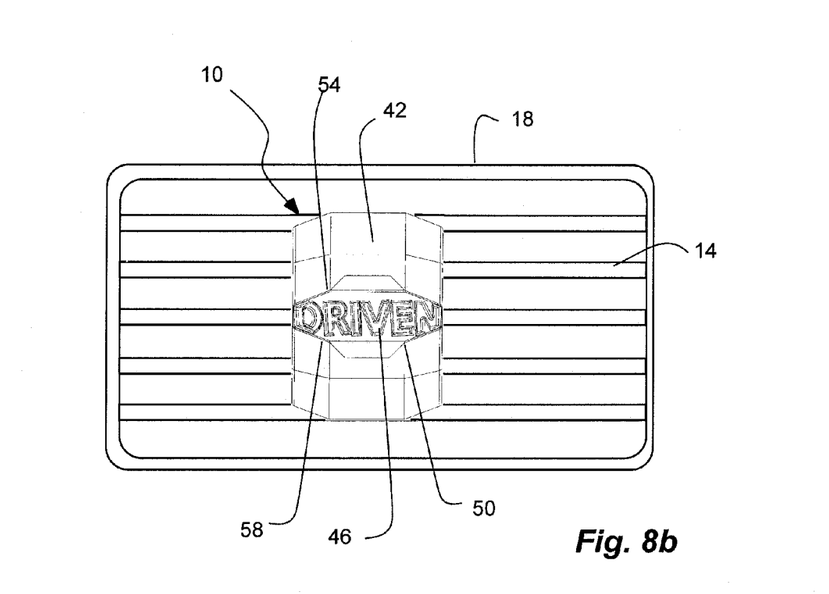
FIG. 8b is a front view of the air freshener device of FIG. 1a utilized with the grill of the air vent.

One or more coherent elastomeric polymer bodies 38 can be coupled to one or both vent rods and extending through the grill with the vent rods. The polymer bodies can be parallel with their respective vent rod, and can be oriented generally horizontal in use. In addition, the polymer bodies can be vertically oriented with respect to one another, with one over the other. The polymer bodies 38 can face away from the gap 30 and away from one another. The polymer bodies 38 can have contoured outward facing surfaces, or top and bottom surfaces, with protrusions and/or indentations to increase the surface area of the polymer bodies. The polymer bodies can also have contoured side surfaces. Like the vent rods, the polymer bodies 38 can have a thickness $t_{pb}$ less than a width $w_{pb}$ of the polymer bodies. The width $w_{pb}$ of the polymer bodies 38 can be equal to the width $w_{vr}$ of the vent rods and the width $w_{af}$ of the air freshener. Fore and/or aft ends of the vent rods have a top or a bottom surface that is substantially flush with a respective top or bottom surface of the polymer bodies. Thus, a top and bottom, or uppermost and lowermost surfaces, of the air freshener are flush across the vent rods with the polymer bodies between the fore and aft ends thereof. A scent material is interspersed within the polymer bodies and is capable of diffusing out of the polymer bodies to surrounding air.

The air freshener 10 can include a scent portion, such as the polymer bodies 38, for providing the desired scent. The scent portion can include a carrier material with a scent material of the desired scent interspersed therein. The term "scent material" is used broadly herein to refer to a material that has a scent that can be discernable or smelled, or even a neutralizing agent. Thus, the scent can be an ascertainable smell used to cover other scents, or a neutral agent that eliminates odors or provides a fresher atmosphere. The scent material disperses or diffuses out of the carrier material into the air or atmosphere where it can be detected, or where it can provide a discernable scent. It is believed that the scent material migrates or diffuses through and out of the carrier material or gel. The scent material can be high in volatile notes, or has high volatility and can vaporize or evaporate at low temperatures. The scent material can include a scented oil. For example, suitable scent material can include pine, berry, vanilla, apple, coconut, cherry, pina colada, etc.

The scent portion and/or the carrier material can include a polymer material, such as a polymer gel, forming a polymer body. The polymer body and/or polymer gel can be elastic and coherent. Thus, the polymer body can elastically deform under normal conditions. The polymer body can be flexible and resilient, such that the body or gel can compress under an applied force, but can substantially return to its original configuration upon removal of the applied force. The polymer gel, or the polymer body, can have a freestanding, self-supported, three-dimensional shape. Thus, the polymer gel or polymer body can be consistent or solid enough to support or maintain its shape in a freestanding manner without a container. The three-dimensional shape can be any desired shape. The polymer gel or body can be considered a solid material that is elastic and coherent, and thus flexible and capable of being deformed, but without being flowable. Thus, the polymer gel or body may have a sufficiently high molecular weight, and/or a sufficiently high viscosity, so that it is a non-flowable gel. In addition, the polymer gel can be considered as stable. Thus, the polymer gel or body can be bendable, but otherwise substantially maintains its form. The polymer body or polymer gel can be characterized as a polymeric material in the glass state with substantially no macroscopic flow. The polymeric material can have a glass transition temperature greater than approximately 110° F. The polymer gel or body can retain its gel-like characteristic over time, without drying or cracking, and without becoming hard or brittle.

In one embodiment, the polymer gel or body can include a polyurethane material or can be a polyurethane gel. The gel or body can be formed by combining a polyurethane material with a scented oil. Surprisingly, it has been found that such a combination provides a desired scent, but without staining or substantially leaking onto a surface. In addition, the scent portion does not undergo a visually ascertainable physical change, such as drying out or cracking. Thus, the scented portion remains aesthetically pleasing.

In some embodiments, a scented oil and a polymerizable monomer can be combined, along with optional initators or other reactants. Isocyanate reaction polymers have shown good results in connection with the present invention. For example, the polymer gel or body and scent material can be a urethane polymerization product of combining a scented oil with a polyether polyol, and then with a diphenylmethane diisocyanate (MDI) prepolymer. Therefore, in some embodiments, the scent material can be a scented oil which participates in the polymerization reaction between polymerization reactants. For example, essential oils such as terpenes and the like can be mixed with polymerization reactants, or even in place of some reactants. Without being bound by any particular theory, it is thought that at least some of the reduction or elimination in residue in the devices of the present invention result from at least partial replacement of mineral oils and/or polyols with scented oils such as those listed herein. Other suitable isocyanates can include, but are not limited to, tolylene diisocyanates, methylene diphenyl isocyanates, hexamethylene diisocyanates, prepolymers thereof, and the like. Those skilled in the art will recognize various other isocyanate reaction polymers, i.e. polyurethanes, which can be suitable for use in connection with the present invention.

Alternatively, the polymer gel or body can include silicone, diffused polyurethane, polyvinylchloride (PVC), ethylene vinyl acetate (EVA), thermoplastic polyurethane (TPU), a polymer encapsulation fragrance delivery platform (Poly-IFF®), thermoplastic elastomer (TPE), polypropylene, ethylene/methacrylic acid (E/MAA) copolymer, in which the MAA groups have been partially neutralized with lithium ions (Surlyn® Dupont), etc.

As a general guideline, the polymer gel or body can be formed of an elastomer such as, but not limited to, urethanes (including polyester and polyether polyol/isocyanate polymerization products), polyacrylates, polybutadienes, ethylene propylene elastomers, silicones, natural and synthetic rubbers, styrene/butadiene block copolymers, and the like. In some embodiments, the polymer gel or body can be formed of a thermoplastic elastomer. Thermoplastic elastomers can be block copolymers such as polyurethanes, polyamides, copolyesters, and styrene-butadiene-styrene polymers. Other thermoplastic elastomers can be elastomer/thermoplastic blends such as ethylene-propylene-diene monomer in an isotactic polypropylene phase or nitrile rubber dispersed in a PVC phase. As used herein, "thermoplastic elastomer" refers to an elastomer which can be heated and processed like thermoplastic materials. Specifically, a thermoplastic elastomer can be heated to a melted or flowable state and then cooled, resulting in reformation of cross-linking and subsequent coherency without a substantial change in mechanical properties such as strength, flexural modulus, elastic modulus, etc.

As used herein, "elastomeric polymer" and "elastomer" may be used interchangeably and refer to a polymeric material which can be mechanically deformed and upon release returns to an original shape. A coherent elastomer is also non-flowable at or near room temperatures.

Although the polymer gel or body is freestanding and self-supporting, it is also flexible and resilient. Thus, the scent portion and carrier material can form a flexible and resilient structure or body that can be selectively deformed and can return substantially to the three-dimensional shape. In addition, the carrier material and polymer gel or body can be light transmissive in at least a translucent manner.

The air freshener 10 or forked body 22 has a head 42 extending away from or opposite the vent rods 26. The forked body, including the head and the vent rods, can be a single, integral, monolithic body formed together of plastic. The head 42 can be disposed adjacent the grill 14 in use. In addition, the head 42 can have indicia 46 thereon facing away from the vent rods and the grill. The indicia can include, by way of example, text or graphics representing logos, instructions, warnings, symbols, etc.

In addition, the head 42 has a flat tab 50 that is flatter or thinner than a height or thickness $t_{af}$ of the air freshener. The flat tab 50 can be broad and thin. In addition, the flat tab can have a broad, gradual curved surface in cross-section perpendicular to the longitudinal axis. The tab 50 can have a pair of opposite finger grip surfaces 54 and 58, or upper and lower surfaces, on opposite sides of the head or tab. The surfaces 54 and 58 are generally parallel with one another. The tab or surfaces have a depth $d_t$ aligned with the vent rods or longitudinal axis of the air freshener that is equal to or greater than a width $w_{af}$ or a height of the pair of vent rods or air freshener, and a width $w_t$ at least substantially equal to the width $w_{vr}$ of the vent rods or air freshener. (The depth of the tab can be defined by the uppermost surface of the ribs described below.) The depth $d_t$ and width $w_t$ of the tab or head facilitate grasping and handling of the air freshener. The finger grip surfaces 54 and 58 can have one or more ribs 62 and/or channels 66. The ribs 62 extend from the surfaces 54 and 58 while the channels 66 penetrate the surfaces or are defined between the ribs. The ribs and/or channels are oriented transverse to the vent rods or longitudinal axis. The ribs and/or channels can be axially arrayed or sequentially spaced in the axial direction. The indicia can be formed on an outer surface or front face of the tab. The front face can be broadly arcuate to increase visibility of the indicia.

Figure 4A:
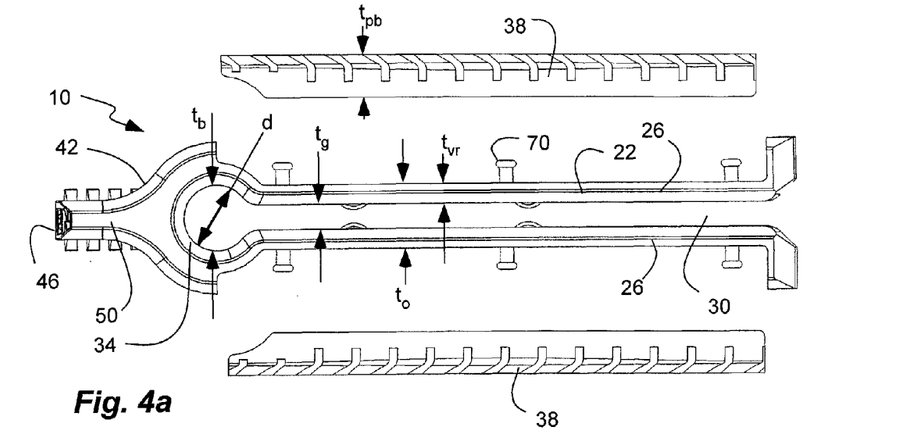
Figure 4B:
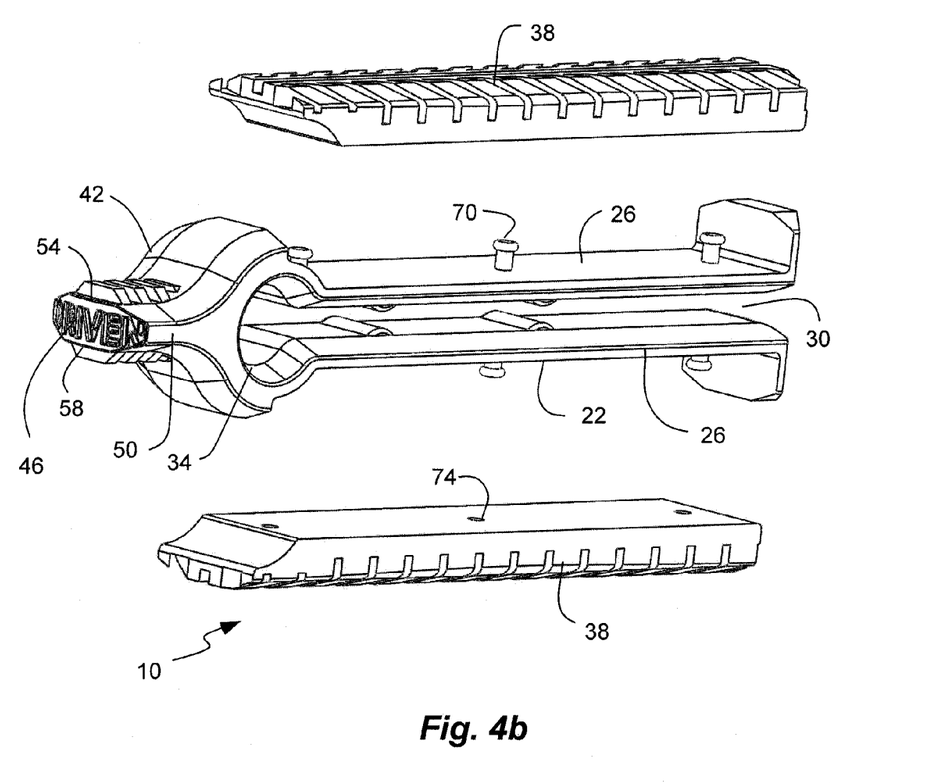

The polymer bodies can be coupled to the vent rods by a plurality of protrusions 70 extending from one into a plurality of apertures 74 in the other.

Various aspects of air fresheners, clips, heads, vent rods, etc. are described and shown in U.S. Pat. Nos. 7,137,570; 7,159,792; 7,293,719; 7,687,037; and 7,687,038; and U.S. patent application Ser. No. 12/623,007; which are herein incorporated by reference in their entirety.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An air freshener device in combination with a grill of an air vent through which air is forced, the device comprising:
   a) a fork body having a pair of vent rods extending through the grill;
   b) at least one coherent elastomeric polymer body coupled to at least one of the pair of vent rods and extending through the grill with the pair of vent rods;
   c) a scent material interspersed within the at least one coherent elastomeric polymer body and capable of diffusing out of the at least one coherent elastomeric polymer body to surrounding air;
   d) a head extending away from the pair of vent rods with the head adjacent the grill and having indicia thereon; and
   e) a pair of opposite finger grip surfaces on opposite sides of the head and having a depth aligned with the pair of vent rods that is equal to or greater than a width or a height of the pair of vent rods.

2. The air freshener device in accordance with claim 1, further comprising:
   each of the pair of opposite finger grip surfaces having at least one rib extending therefrom and oriented transverse to the pair of vent rods.

3. The air freshener device in accordance with claim 1, further comprising:
   each of the pair of opposite finger grip surfaces having at least one channel penetrating therein and oriented transverse to the pair of vent rods.

4. The air freshener device in accordance with claim 1, wherein the pair of opposite finger grip surfaces have a width at least substantially equal to a width of the pair of vent rods, and a depth equal to greater than the width of the pair of vent rods.

5. The air freshener device in accordance with claim 1, further comprising:
   a gap between the pair of vent rods; and
   a genesis of the gap being enlarged with respect to the gap.

6. The air freshener device in accordance with claim 1, wherein at least one of the pair of vent rods has fore and aft ends with a top or bottom surface substantially flush with a respective top or bottom surface of the at least one coherent elastomeric polymer body.

7. The air freshener device in accordance with claim 1, wherein the at least one coherent elastomeric polymer body is coupled to at least one of the pair of vent rods by a plurality of protrusions extending from one of the at least one coherent elastomeric polymer body or the at least one of the pair of vent rods into a plurality of apertures in another of the at least one coherent elastomeric polymer body or the at least one of the pair of vent rods.

8. The air freshener device in accordance with claim 1, wherein the at least one coherent elastomeric polymer body has a width equal to a width of the pair of vent rods.

9. An air freshener device, comprising:
   a) a head with indicia;
   b) a clip coupled to the head extending perpendicularly outward from the head, and sized and shaped to be inserted into a vehicle air vent and clipped to a vehicle air vent cover such that the head is adjacent the vehicle air vent, and including a pair of vent rods sized and shaped to be inserted into the vehicle air vent and having a plurality of protrusions;
   c) a pair of coherent elastomeric polymer bodies having a plurality of apertures, each one of the pair of coherent elastomeric polymer bodies coupled to a different one of the pair of vent rods via coupling of the plurality of apertures with the plurality of protrusions, and insertable into the vehicle air vent with the pair of vent rods;
   d) a scent material, interspersed within the pair of coherent elastomeric polymer bodies, capable of diffusing out of the pair of coherent elastomeric polymer bodies to surrounding air; and
   e) a pair of opposite finger grip surfaces on opposite sides of the head with protrusions or indentations or both to assist gripping the pair of opposite finger grip surfaces.

10. The air freshener device in accordance with claim 9, further comprising:
    each of the pair of opposite finger grip surfaces having at least one rib extending therefrom and oriented transverse to the pair of vent rods.

11. The air freshener device in accordance with claim 9, further comprising:
    each of the pair of opposite finger grip surfaces having at least one channel penetrating therein and oriented transverse to the pair of vent rods.

12. The air freshener device in accordance with claim 9, wherein the pair of opposite finger grip surfaces have a width at least substantially equal to a width of the pair of vent rods, and a depth equal to greater than the width of the pair of vent rods.

13. The air freshener device in accordance with claim 9, further comprising:
    a gap between the pair of vent rods; and
    a genesis of the gap being enlarged with respect to the gap.

14. The air freshener device in accordance with claim 9, wherein at least one of the pair of vent rods has fore and aft ends with a top or bottom surface substantially flush with a respective top or bottom surface of the pair of coherent elastomeric polymer bodies.

15. The air freshener device in accordance with claim 9, wherein the pair of coherent elastomeric polymer bodies has a width equal to a width of the pair of vent rods.

16. An air freshener device in combination with a grill of an air vent through which air is forced, the device comprising:
    a) a fork body having a pair of vent rods extending through the grill;
    b) a gap between the pair of vent rods;
    c) an enlarged genesis of the gap being enlarged with respect to the gap;
    d) a pair of coherent elastomeric polymer bodies each coupled to a different one of the pair of vent rods and extending through the grill with the pair of vent rods and each facing away from the gap;
    e) a scent material interspersed within the pair of coherent elastomeric polymer bodies and capable of diffusing out of the pair of coherent elastomeric polymer bodies to surrounding air;
    f) a head extending away from the pair of vent rods with the head adjacent the grill and having indicia thereon; and
    g) a pair of opposite finger grip surfaces on opposite sides of the head parallel with one another and having a depth aligned with the pair of vent rods that is equal to or greater than a width or a height of the pair of vent rods and a width at least substantially equal to the width of the pair of vent rods; and
    h) each of the pair of opposite finger grip surfaces having at least one rib extending therefrom or at least one channel penetrating therein and oriented transverse to the pair of vent rods.

17. The air freshener device in accordance with claim 16, wherein at least one of the pair of vent rods has fore and aft ends with a top or bottom surface substantially flush with a respective top or bottom surface of one of the pair of coherent elastomeric polymer bodies.

18. The air freshener device in accordance with claim 16, wherein the pair of coherent elastomeric polymer bodies is coupled to the pair of vent rods by a plurality of protrusions extending from one into a plurality of apertures in another.

19. The air freshener device in accordance with claim 16, wherein the pair of coherent elastomeric polymer bodies has a width equal to a width of the pair of vent rods.

\* \* \* \* \*